(12) United States Patent
Kuiper et al.

(10) Patent No.: US 10,874,506 B2
(45) Date of Patent: Dec. 29, 2020

(54) INTRAOCULAR LENS WITH REINFORCING LAYER

(71) Applicant: Verily Life Sciences LLC, South San Francisco, CA (US)

(72) Inventors: Stein Kuiper, Pacifica, CA (US); Daniel Otts, Pleasanton, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 79 days.

(21) Appl. No.: 16/258,916

(22) Filed: Jan. 28, 2019

(65) Prior Publication Data
US 2019/0231519 A1 Aug. 1, 2019

Related U.S. Application Data

(60) Provisional application No. 62/623,807, filed on Jan. 30, 2018.

(51) Int. Cl.
| | | |
|---|---|---|
| A61F 2/16 | (2006.01) |
| G02C 7/08 | (2006.01) |
| G02B 26/00 | (2006.01) |
| B29D 11/02 | (2006.01) |
| B29D 11/00 | (2006.01) |
| A61F 2/48 | (2006.01) |

(52) U.S. Cl.
CPC .......... *A61F 2/1648* (2013.01); *A61F 2/1635* (2013.01); *B29D 11/023* (2013.01); *G02B 26/005* (2013.01); *G02C 7/085* (2013.01); *A61F 2002/482* (2013.01); *A61F 2250/0002* (2013.01); *A61F 2250/0018* (2013.01); *A61F 2250/0043* (2013.01); *A61F 2250/0056* (2013.01); *B29D 11/00817* (2013.01)

(58) Field of Classification Search
CPC ................. G02C 7/085; G02B 26/005; A61F 2250/0018
See application file for complete search history.

(56) References Cited

U.S. PATENT DOCUMENTS

| | | |
|---|---|---|
| 7,499,223 B2 | 3/2009 | Berge et al. |
| 8,157,797 B2 | 4/2012 | Boukhny et al. |
| 8,361,492 B2 | 1/2013 | Tauber et al. |
| 8,466,366 B2 | 6/2013 | Srinivas et al. |
| 8,906,088 B2 | 12/2014 | Pugh et al. |
| 9,195,073 B2 | 11/2015 | Fritsch et al. |

(Continued)

FOREIGN PATENT DOCUMENTS

| | | |
|---|---|---|
| EP | 2239600 A1 | 10/2010 |
| WO | 2007/107589 A1 | 9/2007 |

(Continued)

OTHER PUBLICATIONS

International Search Report and Written Opinion dated May 20, 2019, issued in corresponding International Application No. PCT/US2019/015720, filed Jan. 29, 2019, 14 pages.

(Continued)

*Primary Examiner* — David H Willse
*Assistant Examiner* — Javier G Blanco
(74) *Attorney, Agent, or Firm* — Christensen O'Connor Johnson Kindness PLLC

(57) ABSTRACT

A flexible intraocular lens including a reinforcing layer disposed on a sidewall of the intraocular lens is described. An example flexible intraocular lens includes a lens body and a reinforcing layer disposed thereon.

15 Claims, 12 Drawing Sheets

(56) References Cited

U.S. PATENT DOCUMENTS

| | | |
|---|---|---|
| 9,414,908 B2 | 8/2016 | Maillard |
| 2012/0075711 A1 | 3/2012 | Pugh et al. |
| 2013/0245754 A1 | 9/2013 | Blum et al. |
| 2014/0002790 A1 | 1/2014 | Pugh et al. |
| 2014/0343387 A1 | 11/2014 | Pugh et al. |
| 2014/0350554 A1 | 11/2014 | Keller |
| 2015/0359626 A1 | 12/2015 | Caffey et al. |
| 2016/0259094 A1 | 9/2016 | Aschwanden et al. |

FOREIGN PATENT DOCUMENTS

| | | |
|---|---|---|
| WO | 2012/137067 A2 | 10/2012 |
| WO | 2016/076523 A1 | 5/2016 |
| WO | 2016/173620 A1 | 11/2016 |

OTHER PUBLICATIONS

Dhinda, M. et al., "Electrowetting without Electrolysis on Self-Healing Dielectrics", Langmuir, Apr. 2011, 7 pages.

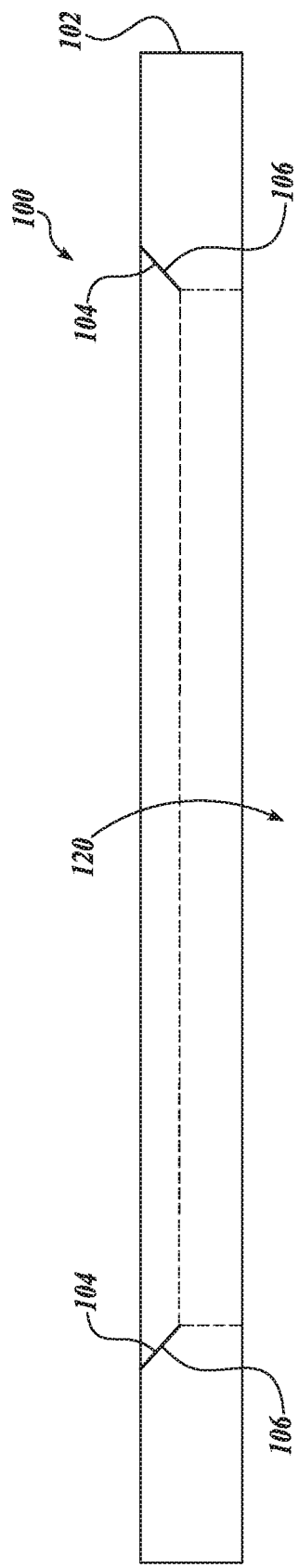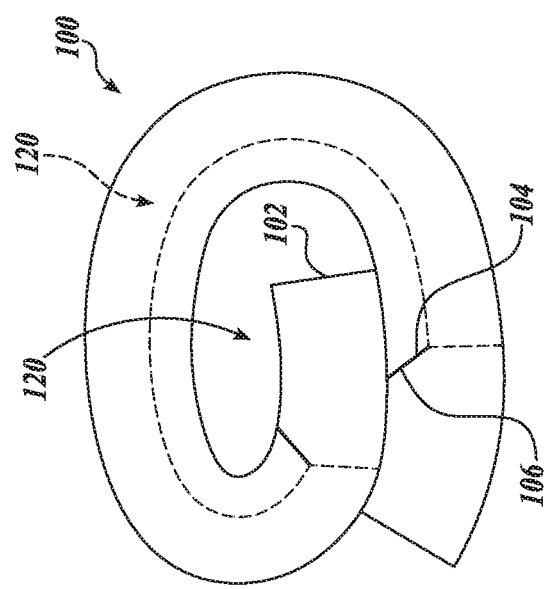

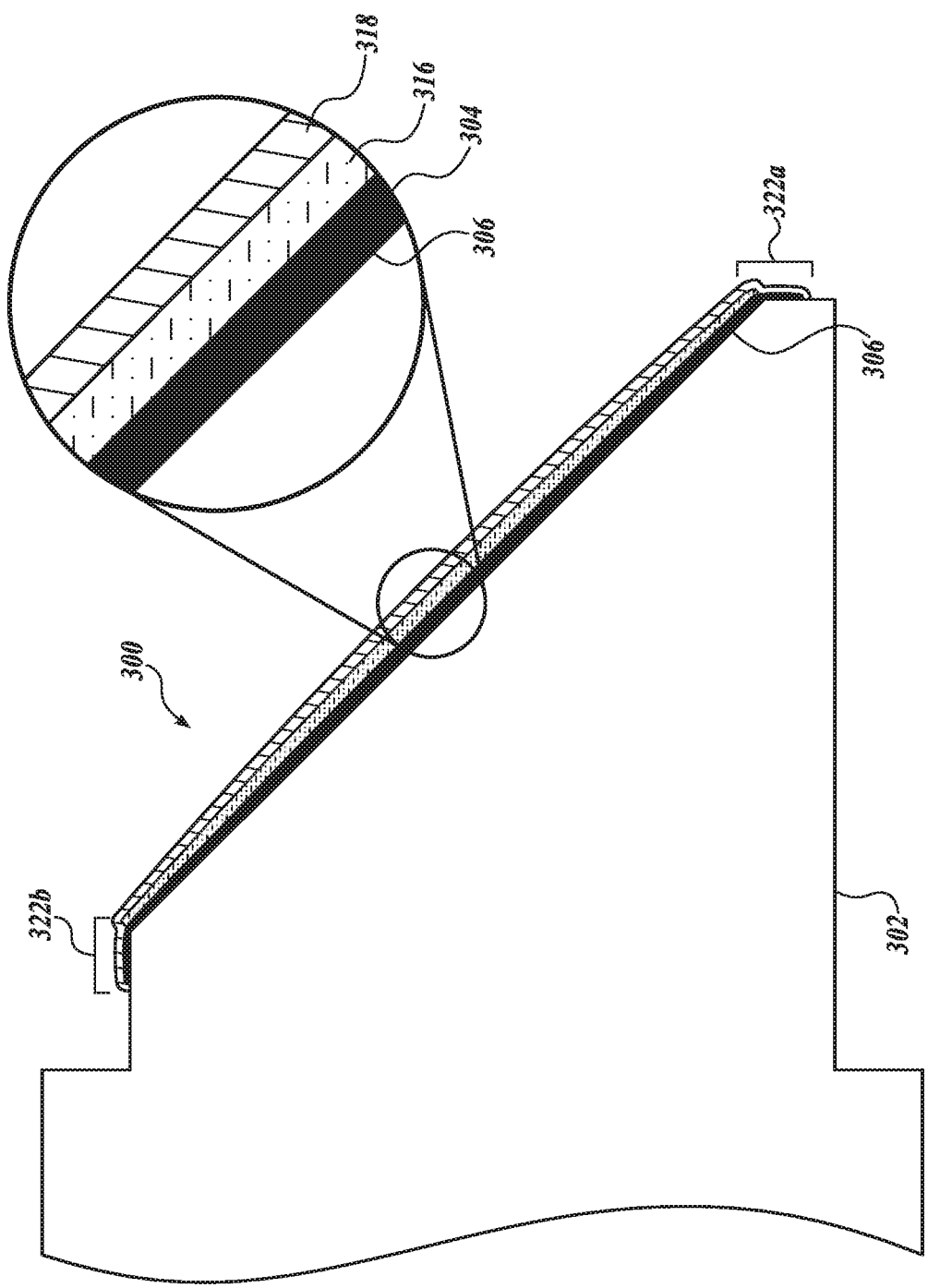

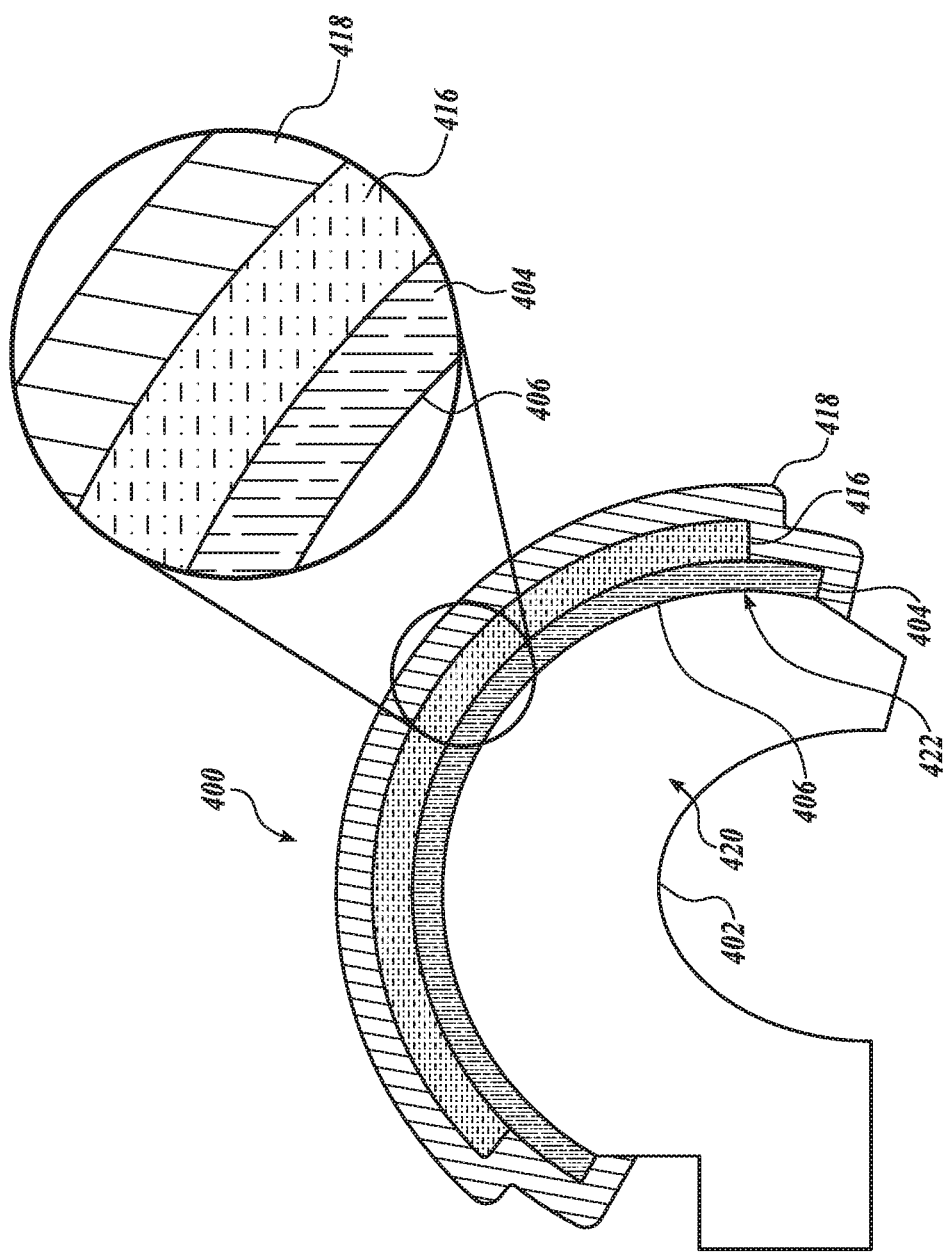

INTRAOCULAR LENS WITH REINFORCING LAYER

This application claims the benefit of U.S. Provisional Application No. 62/623,807, filed Jan. 30, 2018, which is hereby incorporated by reference in its entirety.

TECHNICAL FIELD

This disclosure relates generally to intraocular lenses and, in particular, but not exclusively, relates to reinforcing layers for electrowetting lenses.

BACKGROUND INFORMATION

Presbyopia treatment may include implantation of a replacement lens. Such lenses, which may also be referred to as intraocular lenses, may provide static or dynamic accommodation, or a combination thereof. Various techniques may be available to provide dynamic accommodation, such as mechanically or electrically controlled accommodation. The accommodation may be provided by actuation of a dynamic optical component that provides multiple levels of optical power. The change in optical power may provide different focal distances to the user via the intraocular lens.

BRIEF DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 1B is a cross-sectional illustration of the intraocular lens of FIG. 1A including a reinforcing layer on an inner surface of the annular body, in accordance with an embodiment of the disclosure;

FIG. 1C is a cross-sectional illustration of the intraocular lens of FIG. 1A, in which the intraocular lens is rolled, in accordance with an embodiment of the invention;

FIG. 3A is a cross-sectional illustration of a portion of an intraocular lens including a reinforcing layer disposed on an inner surface of an annular body, in accordance with an embodiment of the disclosure;

FIG. 4 is a cross-sectional illustration of a portion of an intraocular lens under tensile and compressive stress, in accordance with an embodiment of the disclosure;

DETAILED DESCRIPTION

Figure 1A:
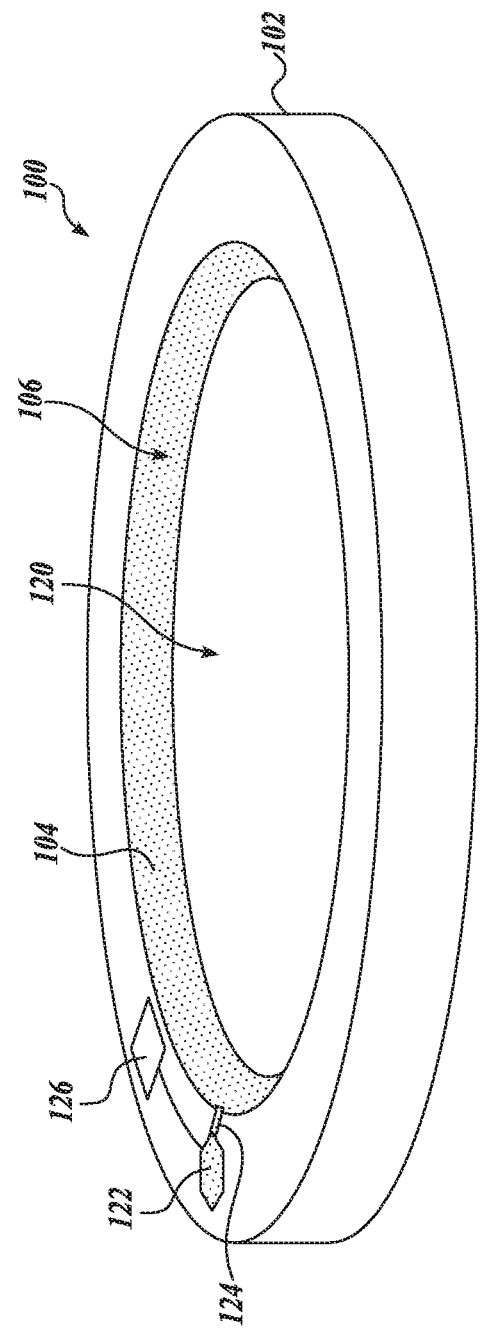
FIG. 1A is an illustration of an intraocular lens including a reinforcing layer on an inner surface of an annular body, in accordance with an embodiment of the disclosure.

Embodiments of an intraocular lens including a reinforcing layer and a method for making a reinforcing layer for an intraocular lens are described herein. For example, the intraocular lens may have an internal cavity defined in part by an aperture of a lens body of the intraocular lens, where a surface of the lens body has the reinforcing layer disposed thereon. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An intraocular lens (IOL) may be implanted in a user's eye to assist in accommodation when the user's lens is no longer able to change focus as desired, for example. The IOL may have static optical power or may have the ability to dynamically accommodate, e.g., alter the optical power of the IOL, so the user may change focus similar to the natural eye. Dynamic accommodation may be provided using an IOL that is capable of changing the shape of an internal lens, which may provide the desired accommodation. While mechanically actuated accommodation may be an option, electrically actuated accommodation may provide better range and response.

Electrically actuated lenses may use electrodes and interconnects within the IOL to provide the voltages, current, and power needed to drive the actuation. One actuation technique of interest is electrowetting. Electrowetting operates by changing surface energy of a dielectric coating on an electrode from hydrophobic to hydrophilic when bias is applied, and vice versa, for example. The change in surface energy may cause an interface between two immiscible liquids of different refractive indices to change shape, thereby providing a lensing effect. A voltage applied to the electrode may attract or repel one of the two immiscible liquids, which causes the shape of the interface to change.

Because the IOL will be implanted into an eye, a small incision in the eye may be desirable. Yet, because the IOL may be a size similar to the original lens, for example, a large incision may be required. However, if the IOL is capable of being rolled into a cylindrical shape or folded, a smaller incision may be possible. In general, most of the materials of the IOL may be amenable to being rolled, but conventional conductors may experience reliability issues due to the stresses of rolling/flexing events. For example, conventional conductors may delaminate from a substrate and/or crack or buckle from the stresses induced from rolling and/or folding. Accordingly, it may further be desirable for the lens body to include a reinforcing layer carrying a flexible conductor.

FIG. 1A is an illustration of an IOL 100 including a reinforcing layer 104 on an inner surface 106 of a lens body 102, in accordance with an embodiment of the disclosure. The illustrated embodiment of the IOL 100 includes a lens body 102, a reinforcing layer 104, a contact pad 122, an interconnect 124, and control electronics 126. As shown, the lens body 102 is an annular body 102 being annulus shaped to define an aperture 120. FIG. 1B is a cross sectional illustration of the intraocular lens 100 of FIG. 1A including the reinforcing layer 104 on the inner surface 106 of the annular body 102, in accordance with an embodiment of the disclosure. In general, the IOL 100 may include other components, such as a flexible conductor, a dielectric layer, optical windows, and a dynamic optic, which are not shown in FIGS. 1A, 1B, and 1C (see, for example, FIGS. 3A-3E). The IOL 100 may be formed from one or more flexible materials, such as flexible, biocompatible, and otherwise non-toxic materials, amenable to implantation into the eye of a user. In some embodiments, the IOL 100 may be able to provide dynamic accommodation to a user based on electrowetting principles. For example, the IOL 100 may include two immiscible fluids, an oil and an electrolyte solution (not shown, see, for example, FIG. 2), for example, that may provide dynamic accommodation by inducing a change in the shape of an interface between the two immiscible fluids in response to an applied voltage, which may provide a lensing behavior. In an embodiment, the two immiscible fluids include an oil and an electrolyte solution. However, the two immiscible fluids can include any pair of fluids that tend to form a mutual interface.

In an embodiment, the IOL 100 includes a flexible conductor and a dielectric layer on inner surface of annular body 102 for applying a voltage to induce lensing behavior. The change in the interface shape may be due to one of the two immiscible fluids, for example a polar fluid, being attracted by an electrostatic field between the flexible conductor and said fluid.

FIG. 1C is an illustration of the intraocular lens 100 of FIG. 1A including a reinforcing layer 104 on an inner surface 106 of the annular body 102, in which the IOL 100 is rolled, in accordance with an embodiment of the disclosure. As above, during implantation the IOL 100 may be rolled, folded, or otherwise deformed, thereby inducing tensile and compressive stresses on portions of the IOL 100, particularly any flexible conductor disposed on the inner surface 106 of the annular body 102. Reinforcing layer 104 carried by the inner surface 106 of annular body 102 has a higher elastic modulus than the flexible material of the annular body 102. In this regard, reinforcing layer 104 reduces tensile stress on any flexible conductor carried by reinforcing layer 104, thereby mitigating or preventing any cracking or buckling of the flexible conductor from the inner surface 106 of the annular body 102. In an embodiment, the reinforcement layer is thin and elastic enough to be bent over a radius of between about 0.5 mm and about 2.0 mm, such as during implantation, without exceeding its yield strain.

FIG. 4 is a cross-sectional illustration of a portion of an IOL 400 under tensile and compressive stress, in accordance with an embodiment of the disclosure. In an embodiment, IOL 400 is an example of IOL 100. In the illustrated embodiment, at least a portion of IOL 400 is bent so that annular body 402, reinforcing layer 404, flexible conductor 416, and dielectric layer 418 assume an arc-like cross-sectional configuration. In an embodiment, such components of IOL 400 assume an arc-like cross-sectional configuration when IOL 400 is rolled, such as during implantation in an eye. As shown, reinforcing layer 404 is carried by an inner surface 406 of the annular body 402. Further, flexible conductor 416 is carried by at least a portion of reinforcing layer 404. When bent into an arc-like cross-sectional configuration, portions of certain components are in compression whereas others are in tension. For example, first portion 420 of the annular body 402 distal from the inner surface 406 of annular body 402 is under compression. In contrast, second portion 422 of the annular body 402 proximate to the inner surface 406 of annular body 402 is under tension. In an embodiment, the reinforcing layer 416 has a higher elastic modulus than the flexible material of the annular body 402, but is generally not stiffer than the annular body 402. In this regard, the reinforcing layer 404 is configured to reversibly bend over a small radius, such as during rolling or folding, and still prevent over-stretching or over-compression of the flexible conductor 416. Accordingly, by including reinforcing layer 404 in IOL 400, cracking or buckling of flexible conductor 416 is mitigated or prevented when portions of IOL 400 are under tension.

Referring back to FIGS. 1A and 1B, annular body 102 may provide mechanical support for the various other features of the IOL 100. For example, the annular body 102 may act as a substrate for such features discussed herein. In some embodiments, the annular body 102 may be a substrate for mounting various electronics, such as the control electronics 126. The control electronics 126 may be coupled to at least provide a voltage to a flexible conductor. While the control electronics 126 are depicted as being mounted to a surface of the annular body 102, in some embodiments, the control electronics 126 are tethered to the annular body 102 and coupled to the contact pad 122. In such an embodiment, the control electronics 126 are mounted to a separate support structure, such as a substrate formed from a material, and implanted in a different area of an eye than the IOL 100.

In general, the annular body 102 may be formed from a material that is amenable to being rolled and/or folded and otherwise amenable to implantation into an eye. In an embodiment, the flexible material is a flexible, biocompatible material chosen from silicones, sol-gels, and AcrySof®. Such flexible, biocompatible materials may be non-toxic in an eye and, in this regard, are amenable to implantation therein. Other flexible biocompatible materials, such as biocompatible hydrogel, silicone, hydrophobic acrylic, fluorinated polymethacrylate, and the like, may also be used. The annular body 102 may be a main structural component of the IOL 100 that provides a platform for other IOL 100 components. The annular body 102 may be flexibly capable of being rolled up and/or folded so that it may be manipulated into a smaller shape to accommodate insertion into an eye through a small incision, e.g., an incision roughly 2 mm in length.

In the embodiment of the IOL 100, the annular body 102 is annulus-shaped, e.g., washer-shaped, having an aperture 120 formed there through. As discussed further herein, while annulus-shaped annular bodies 102 are discussed, it is understood that lens bodies of the present disclosure include lens bodies having other shapes. The aperture 120 may provide an optical path for the IOL 100. In some embodiments, optical windows may be placed over the aperture 120 on both an anterior and a posterior surface of the annular body 102 (not shown, see FIG. 2 for an example). While not shown in the IOL 100, the annular body 102 may include a recess along an inner edge of the annular body 102 to provide a location for mounting and centering one or more optical windows (See also FIG. 2). The recess may provide an area to strengthen the mounting of the optical windows and provide a seal between the two.

The aperture 120 may be defined by an inner surface 106, e.g., a sidewall, of the annular body 102. In the illustrated embodiment of the IOL 100, the inner surface 106 includes the reinforcing layer 104 disposed thereon. The inner surface 106 may be at a non-orthogonal angle, e.g., oblique angle, to anterior and/or posterior surfaces of the annular body 102. For example, the sidewall may be at a 45° angle to at least one of the anterior or posterior surfaces of the annular body 102. In general, performance aspects of the IOL 100 may determine an oblique angle of the sidewall with respect to a top or bottom surface of the annular body 102, and angles other than 45° are within the scope of the present disclosure. In some embodiments, the shape of the inner surface 106 may form a conical frustum.

Figure 2:
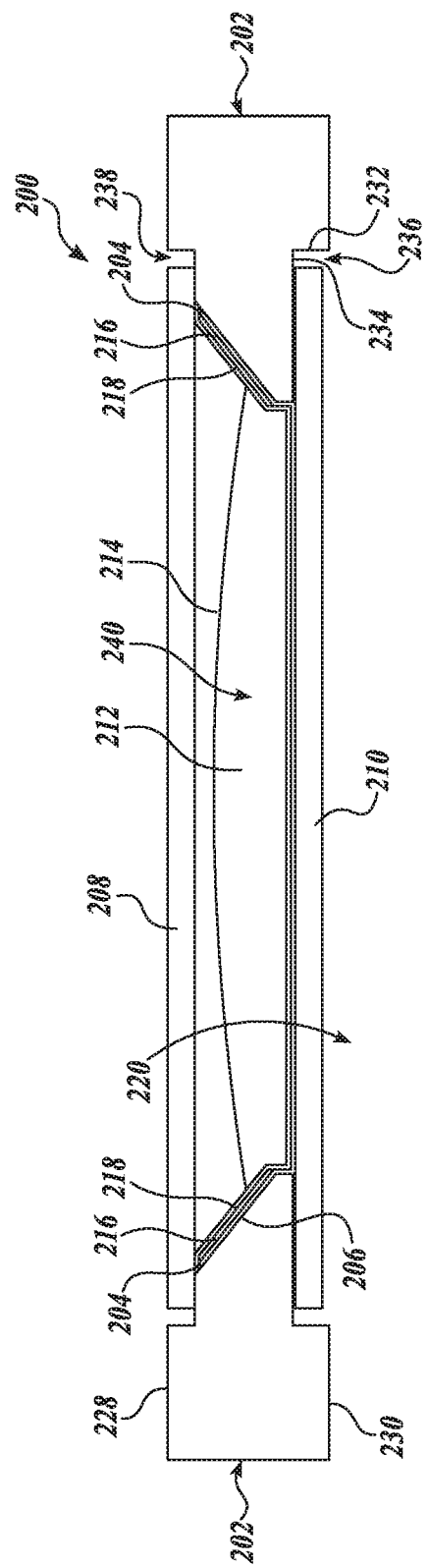
FIG. 2 is a cross-sectional illustration of an intraocular lens including a reinforcing layer on an inner surface, in accordance with an embodiment of the disclosure.

FIG. 2 is a cross-sectional illustration of an IOL 200 including a reinforcing layer 204 on an inner surface 206 of a lens body 202, shown here as an annular body 202, in accordance with an embodiment of the disclosure. The IOL 200 may generally be similar to the IOL 100. The illustrated example of the IOL 200 is shown to include an annular body 202 having at least one inner surface 206, a reinforcing layer 204 carried by the at least one inner surface 206, a conductor 216, such as a flexible conductor 216, carried by at least a portion of the reinforcing layer 204, a dielectric layer 218 disposed over the flexible conductor 216, a first optical window 208, a second optical window 210, and two or more immiscible liquids 212 and 214 disposed in a cavity 240 defined by inner surface 206 and optical windows 208 and 210. In an embodiment, the two or more immiscible fluids include a polar fluid 212 and a non-polar fluid 214. The IOL 200 may provide dynamic accommodation to a user induced by electrowetting principles.

The annular body 202 may be annulus-shaped and have an aperture 220 formed through it. The inner surface 206 of the annular body 202 may at least partially define the aperture 220, along with other internal facets of the annular body 202. The annular body 202 may provide structural support for the reinforcing layer 204, the flexible conductor 216, the dielectric layer 218, one or more contact pads (not shown, see FIG. 1) coupled to the flexible conductor 216, and the optical windows 208 and 210. Additionally, the annular body 202 may provide a substrate for electronics and/or power sources for providing charge to at least the flexible conductor 216 to induce the electrowetting-based dynamic accommodation of the IOL 200.

The annular body 202 may further have a recess formed on an inner edge of both the anterior surface 228 and the posterior surface 230 that encircle the aperture 220. The recesses 236 and 238 may provide surfaces for mounting and sealing the optical windows 208 and 210 to the annular body 202. The recess 236 may be defined by surfaces 232 and 234 formed into the posterior surface 230, which may be mirrored on the anterior surface 228. In some embodiments, the recess 238 formed into the anterior surface 228 and the recess 236 formed into the posterior surface 230 may be different and provide different surface areas of the annular body 202. Additionally, the inner surface 206, which extends from recessed anterior surface 228 and posterior surface 230 of the annular body 202, may be truncated at an innermost point that defines the smallest diameter of the aperture 220.

The annular body 202 may comprise one or more flexible materials. In an embodiment, the flexible material is a flexible biocompatible material chosen from silicone, sol-gels, polymers, and the like. In an embodiment, the annular body 202 comprises AcrySof® produced by Alcon of Fort Worth, Tex. In an embodiment, the flexible material is amenable to implantation in an eye allowing the IOL 200 to be implanted into the eye of a user, such as by rolling and/or folding.

The flexible conductor 216 may include one or more flexible, electrically conductive components. In an embodiment, the one or more electrically-conductive components include a self-healing electrode material. In certain embodiments, flexible conductor 216, including self-healing materials, forms a thin, impermeable oxide layer that prevents electric current from flowing. Such oxide layers limit or prevent electric current flow through gaps or cracks in the dielectric layer. In an embodiment, the flexible conductor 216 includes a metal chosen from gold, titanium, niobium, vanadium, hafnium, tungsten, and combinations thereof. Such a flexible conductor 216 is suitable to stretch, such as during rolling, folding, and the like, during implantation of the IOL 200 without tearing or otherwise breaking.

In an embodiment, the conductor 216 includes a ductile conductive material, such as a ductile metal. In an embodiment, the ductile metal is chosen from aluminum, tantalum, and combinations thereof. Such ductile metals may go over their plastic limits when, for example, the IOL 200 is rolled, folded, and the like during implantation. However, as the IOL 200 unfolds to assume an unfolded configuration, the reinforcing layer 204 pulls the ductile conductive material back into shape, again over its plastic limit.

In the illustrated embodiment, the first optical window 208 and second optical window 210 are mounted to the anterior side 228 and posterior side 230 of the annular body 202, respectively. While anterior and posterior are used herein to discuss the opposite sides of the annular body 202, for example, the anterior and posterior designations do not necessarily denote any directionality to the IOL 200 and are used merely as a reference with respect FIG. 2. In an embodiment, the posterior side 230 of the annular body 202 is configured to face the retina of an eye when implanted in an eye, whereas the anterior side 228 of the annular body 202 is configured to face the cornea of an eye when implanted in an eye.

The optical windows 208 and 210 may be transmissive to visible and other light and disposed to cover the aperture 220. The optical windows 208 and 210 may be with or without optical power. In certain embodiments, one or both of the optical windows 208 and 210 provide static optical power to the IOL 200, which may be affected by the electrowetting-based dynamic accommodation of the IOL 200. In certain embodiments, the optical windows 208 and 210 do not have any optical power. In either embodiment, the optical windows 208 and 210 may be coupled to the annular body 202 to retain the two immiscible liquids 212 and 214 within cavity 240. In an embodiment, the cavity 240 is defined, in part or in whole, by the aperture 220 and the optical windows 208 and 210.

In an embodiment, the one or more of the optical windows 208 and 210 may be integrally coupled with the annular body 202. Furthermore, in an embodiment, one of the optical windows 208 and 210 may be formed in single step along with the annular body 202, such as by co-molding the annular body 202 and one of the optical windows 208 and 210, as discussed further herein with respect to method 500. In an embodiment, the reinforcing layer 204 and the dielectric layer 218 are disposed on one or more of optical windows 208 and 210 co-molded with annular body 202.

In an embodiment, one or more of the optical windows 208 and 210 are electrically conductive. For example, optical window 208, which the inner surface 206 faces, may be electrically conductive. In an embodiment, a transparent conductor, such as indium tin oxide (ITO), is disposed on at least a portion of the optical window 208. In this regard, the IOL 200 is configured to generate a potential difference between the flexible conductor 216 and a polar fluid, such as fluid 212, across the dielectric layer 218, which may be used to generate electrowetting-induced accommodation.

In an embodiment, the IOL 200 includes at least one dielectric layer 218 disposed over the flexible conductor 216. In an embodiment, the dielectric layer 218 is in direct contact with the flexible conductor 216. In an embodiment, the dielectric layer 218 covers the entire flexible conductor 216. In this regard, the dielectric layer 218 is configured to prevent electrical shorts between, for example, the flexible conductor 216 and the polar fluid 212. In an embodiment, prevention of electrical shorts allows charge to build up on, for example, the dielectric layer 218 and an optical power of the IOL 200 to change.

As shown in FIG. 2, the inner surface 206 of the annular body 202 is at a non-normal angle relative to anterior surface 228 and posterior surface 230 of the annular body 202. In some embodiments, the inner surface 206 is shaped like a conical frustum. In some embodiments, the inner surface 206 is at a 45° angle relative to anterior surface 228 and the posterior surface 230 of the annular body 202.

In operation, charge may be provided to the flexible conductor 216 by generating a potential difference between the flexible conductor 216 and the polar fluid 212. The potential difference may cause charge to build up on the flexible conductor 216, which may cause attraction of the polar fluid 212 towards the flexible conductor 216, or encapsulating dielectric layers 218. This attractive force may cause the polar fluid 212 in the cavity 240 to change shape in response. The change in their interface may cause a lensing effect, which may change an optical power of the IOL 200.

Figure 7:
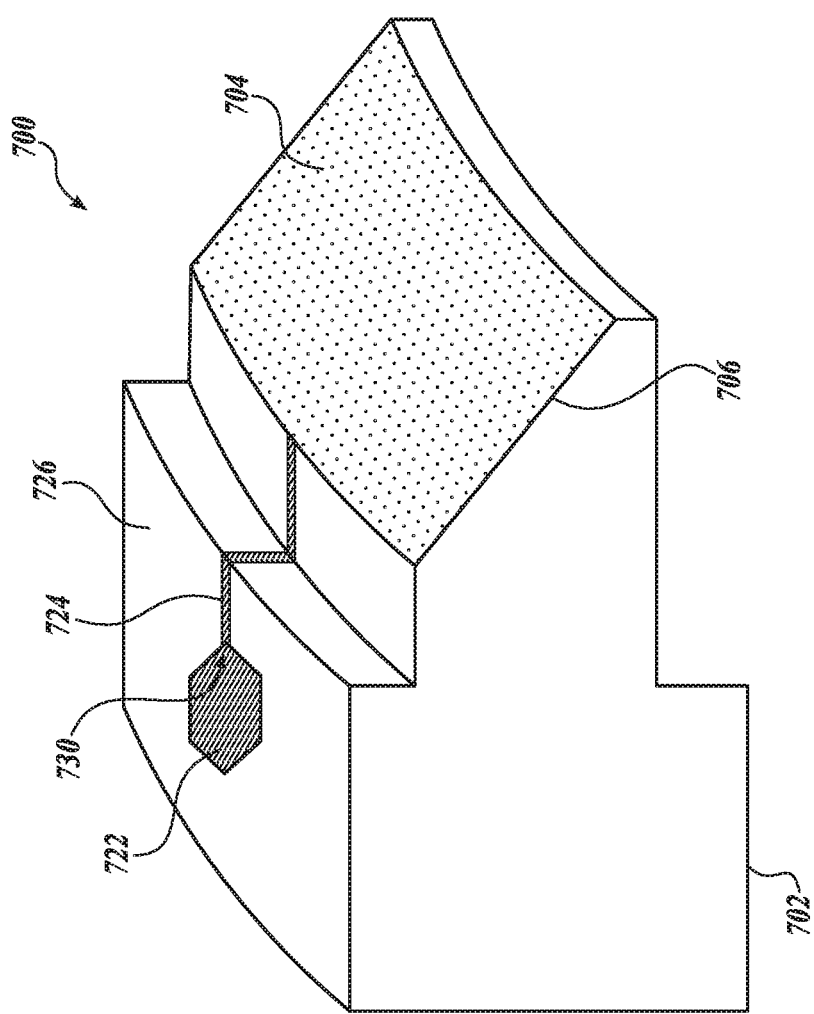
FIG. 7 is a perspective, cross-sectional illustration of an annular body of an intraocular lens having a number of reinforcing layers disposed thereon, in accordance with an embodiment of the disclosure.

In an embodiment, a reinforcing layer of the IOLs described herein is a first reinforcing layer and the IOL includes at least a second reinforcing layer. In that regard, attention is directed to FIG. 7, which is a perspective, cross-sectional illustration of an annular body 702 of an IOL 700 having a number of reinforcing layers 704 and 730 disposed thereon, in accordance with an embodiment of the disclosure. The IOL 700 may be an example of IOLs 100, 200, and 400. In the illustrated embodiment, IOL 700 includes an annular body 702 having at least one inner surface 706, a first reinforcing layer 704 carried by the at least one inner surface 706, anterior side 726 of the annular body 702, and second reinforcing layer 730 having two portions 722 and 724 configured to carry a contact pad and an interconnect, respectively (not shown, see FIG. 1). As above, in certain embodiments the IOL 700 disclosed herein includes electronic components other than accommodation actuators, such as contact pads, interconnects, and control electronics. When such electronic components are disposed on flexible components of the IOL 700, such as annular ring 702, it may be advantageous to include a second reinforcing layer 730 on the flexible component to carry the electronic components in order to prevent or mitigate cracking or delamination of such electrical components.

FIG. 3A is a cross-sectional illustration of a portion of an IOL 300 including a reinforcing layer 304 disposed on an inner surface 306 of an annular body 302, in accordance with an embodiment of the disclosure. The IOL 300 may be an example of IOLs 100, 200, 400, and 700. In the illustrated embodiment of FIG. 3A, the IOL 300 is shown to include an annular body 302, a reinforcing layer 304, a flexible conductor 316, and a dielectric layer 318.

The annular body 302 may be substantially similar to the annular bodies 202 and 102, in that it provides mechanical support for the reinforcing layer 304 and one or more optical windows (not shown, see FIG. 2). In an embodiment, the annular body 302 comprises a flexible material and may be used as a portion of an implantable intraocular lens 300, for example. In an embodiment, annular body 302 includes at least one inner surface 306.

In an embodiment, IOL 300 comprises a reinforcing layer 304 carried by the inner surface 306, wherein the reinforcing layer 304 has a higher elastic modulus than the flexible material of the annular body 302. In an embodiment, the flexible conductor 316 is carried by at least a portion of the reinforcing layer 304. When, for example, IOL 300 is rolled, folded, or otherwise deformed, portions of the flexible material stretch. The reinforcement layer 304 resists or decreases such stretching within the reinforcement layer 304 and, and for example, in the flexible conductor 316, thereby reducing tensile stresses applied to the flexible conductor 316. In this regard, the reinforcing layer 304 is configured to mitigate or otherwise prevent cracking or buckling of the flexible conductor 316.

In an embodiment, the flexible conductor 316 covers less than all of the reinforcing layer 304. In that regard, attention is directed to end portions 322a and 322b of reinforcing layer 304 in which the reinforcing layer 304 extends beyond the flexible conductor 316. As illustrated, the flexible conductor does not cover all of the reinforcing layer 304. As above, when IOL 300 is rolled, folded, or otherwise deformed, tensile stresses can be transferred from portions of the IOL 300, such as the annular body 302, to other portions, such as the flexible conductor 316. In the absence of such end portions 322a and 322b, which extend beyond the flexible conductor 316, portions of the flexible conductor 316 may be exposed to tensile stresses from, for example, the flexible material of the annular body 302.

In an embodiment, reinforcing layer 304 comprises a polymeric material having a higher elastic modulus than the flexible material. In an embodiment, the polymeric material is chosen from a polyimide, a polyetherimide, a polymethylmethacrylate, a polyacrylate, a thiol-ene, an epoxy, polyethylene terephthalate, and combinations thereof.

In an embodiment, the reinforcing layer 304 comprises a polymeric material having a higher elastic modulus than the flexible material and having a thickness between about 5 μm and about 75 μm. In an embodiment, the reinforcing layer 304 comprises a polymeric material having a higher elastic modulus than the flexible material and having a thickness between about 7.5 μm and about 50 μm. In an embodiment, the reinforcing layer 304 comprises a polymeric material having a higher elastic modulus than the flexible material and having a thickness between about 10 μm and about 25 μm.

In an embodiment, the polymeric material having a higher elastic modulus than the flexible compatible material is in direct, conformal contact with the at least one inner surface 306 of the annular body 302.

Still referring to FIG. 3A, dielectric layer 318 is shown disposed over flexible conductor 316. In the illustrated embodiment, dielectric layer 318 is directly disposed over flexible conductor 316 and is in direct, conformal contact with flexible conductor 316. In an embodiment, dielectric layer 318 covers all of flexible conductor 316, thereby preventing electrical shorts between, for example, flexible conductor 316 and a polar fluid (not shown, see, for example, FIG. 2).

In an embodiment, reinforcing layers of the IOLs described herein comprise fibers. In that regard, attention is directed to FIG. 3B, which is a cross-sectional illustration of a portion of an IOL 300 including a reinforcing layer 304 including fibers 320 disposed on an inner surface 306 of an annular body 302, in accordance with an embodiment of the disclosure. In an embodiment, the reinforcing layer 304 including fibers 320 has a higher elastic modulus than a flexible material of the annular body 302. In an embodiment, the fibers 320 are flexible, but not generally stretchable. This can be achieved by keeping the reinforcing layer 304 very thin. In an embodiment, reinforcing layer 304 has a thickness of between about 0.5 mm and about 2.0 mm. In this regard, the fibrous reinforcing layer 304 is amenable to being rolled, bent, and otherwise deformed, while not stretching as much as, for example, the flexible material of annular body 302 during such deformation.

In an embodiment, the reinforcing layer 304 comprises fibers 320 embedded in a polymeric matrix 324. The polymeric matrix 324 aids in adhering the fibers 320 together and to the inner surface 306 of the annular body 302. In an embodiment, the polymeric matrix 324 is a crosslinked polymeric matrix 324, such as an epoxy. In an embodiment, the polymeric matrix 324 is cured by exposure to ultraviolet light and/or heating. In an embodiment, the polymeric matrix 324 is chosen from a urethane, a silicone, and a methacrylate. In an embodiment, the polymeric matrix 324 comprises hydroxyethylmethacrylate. In an embodiment, the polymeric matrix 324 comprises diethyleneglycoldimethacrylate. In an embodiment, the polymeric matrix 324 comprises polyimide or polyetherimide.

Furthermore, by embedding the fibers 320 in a polymeric matrix 324, the fibers 320 may extend through, for example, the flexible conductor 316 and the dielectric layer 318 to a lesser extent. In this regard, the polymeric matrix 324 reduces or eliminates electrical shorts between, for example, the flexible conductor 316 and the polar fluid and increases smoothness of the dielectric layer 318.

In an embodiment, fibers 320 extend into the biocompatible material of the annular body 302 (not shown, see, for example, FIG. 3C), thereby improving adhesion between the reinforcing layer 304 and the annular body 302.

In an embodiment, the reinforcing layer 304 comprises fibers 320 and a polymeric matrix 324 both having a higher elastic modulus than the flexible compatible material.

In an embodiment, the fibers 320 comprise one or more metal oxides. In an embodiment, the fibers 320 comprise aluminum oxide. In an embodiment, the fibers 320 comprise silicon dioxide.

In an embodiment, the fibers 320 are electrically conducting. In an embodiment, the fibers 320 include carbon nanotubes. It may be desirable to cover or coat such conductive fibers 320 with a dielectric layer 318 to prevent electrical conduction between the conductive fibers 320 and, for example, one of the immiscible fluids, such as a polar fluid.

In an embodiment, the fibers 320 are nanofibers 320 having an average smallest dimension of between about 1 nm and about 1,000 nm. In an embodiment, the nanofibers 320 have an average smallest dimension between about 1 nm and about 400 nm. In an embodiment, the nanofibers 320 have an average smallest dimension between about 2 nm and about 10 nm. In this regard, the fibers 320 do not scatter visible light and, thus, the reinforcing layer 304 is, in an embodiment, optically transmissive. Accordingly, in an embodiment, the nanofibers 320 are disposed on or embedded in an inner surface 306 of the annular body 302 and/or on or embedded in an optical window (not shown, see, for example, FIG. 2) or other portion of IOL 300 configured to be in an optical path when implanted.

In an embodiment, fibers 320 have a refractive index similar to the flexible material. In that regard, fibers 320 are generally not visible. In an embodiment, fibers 320 comprise silica and the flexible material of the annular body 302 comprises a silicone.

Furthermore, nanofibers 320 disposed on the inner surface 306 of the annular body 302 or embedded in a portion of the annular body 302 proximate to the inner surface 306 of the annular body 302 can provide a smoother surface for the flexible conductor 316 and the dielectric layer 318. As discussed herein, in certain embodiments the dielectric layer 318 is configured to modulate the optical power of IOL 300 through an electrowetting effect. A smooth dielectric layer 318, such as one carried by a reinforcing layer 304 and comprising nanowires, can be configured to evenly modulate the optical power of IOL 300.

In an embodiment, the flexible conductor of an IOL of the present disclosure is disposed on fibers. In this regard, attention is directed to FIG. 3C, which is a cross-sectional illustration of a portion of an IOL 300 including a reinforcing layer 304 including fibers 320 disposed on an inner surface 306 of an annular body 302, in accordance with an embodiment of the disclosure. In the illustrated embodiment, fibers 320 are disposed on the inner surface 306 of the annular body 302. In an embodiment and as illustrated, the flexible conductor 316 is disposed directly on fibers 320. In an embodiment, the fibers 320 are not embedded in a polymeric matrix. In an embodiment, the flexible conductor 316 conformably coats fibers 320, thus improving electrical conductivity of the flexible conductor 316 and improving the bond between the fibers 320 and the flexible conductor 316.

Figure 3B:
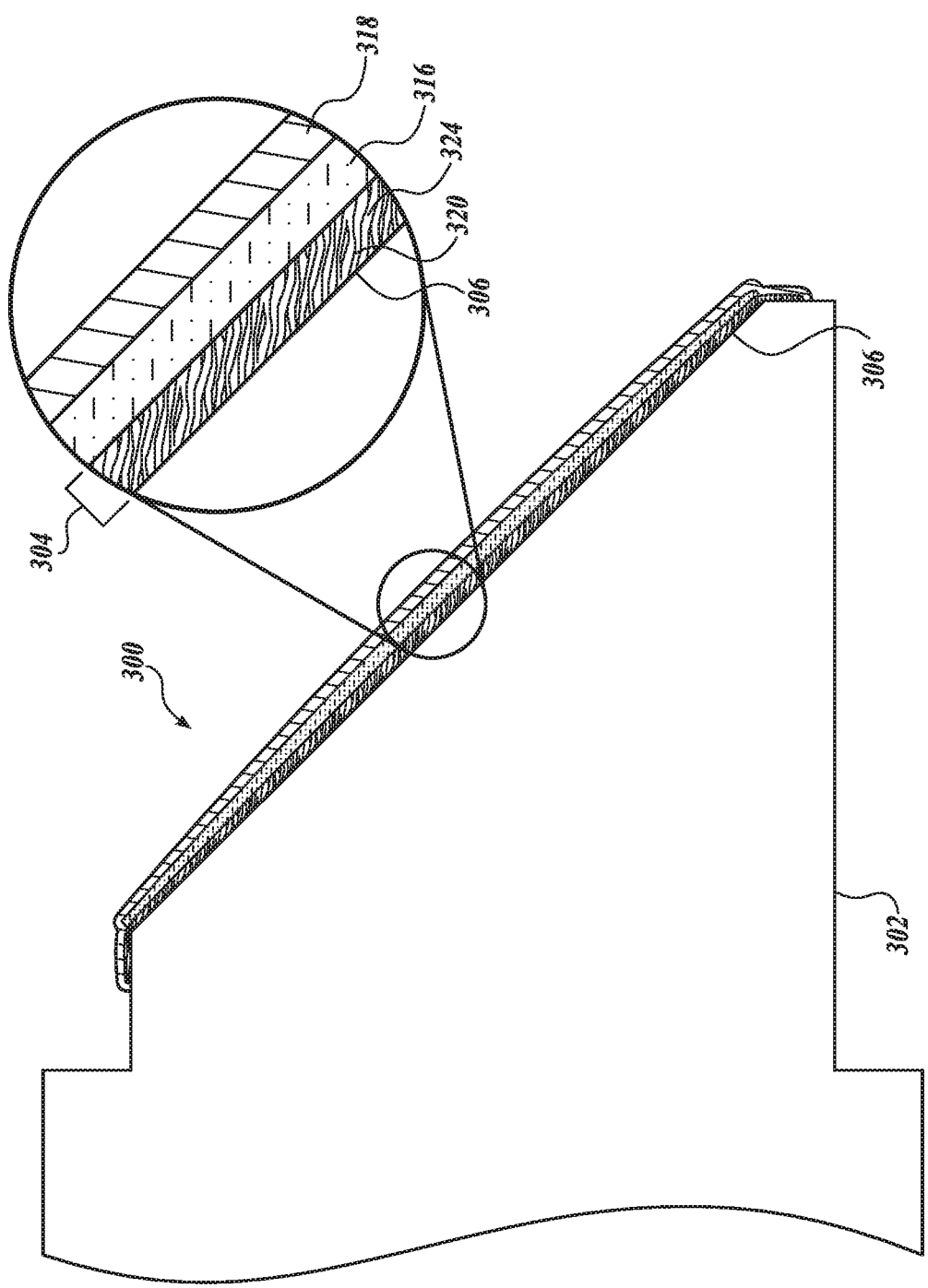
FIG. 3B is a cross-sectional illustration of a portion of another intraocular lens including a reinforcing layer including fibers disposed on an inner surface of an annular body, in accordance with an embodiment of the disclosure.
Figure 3C:
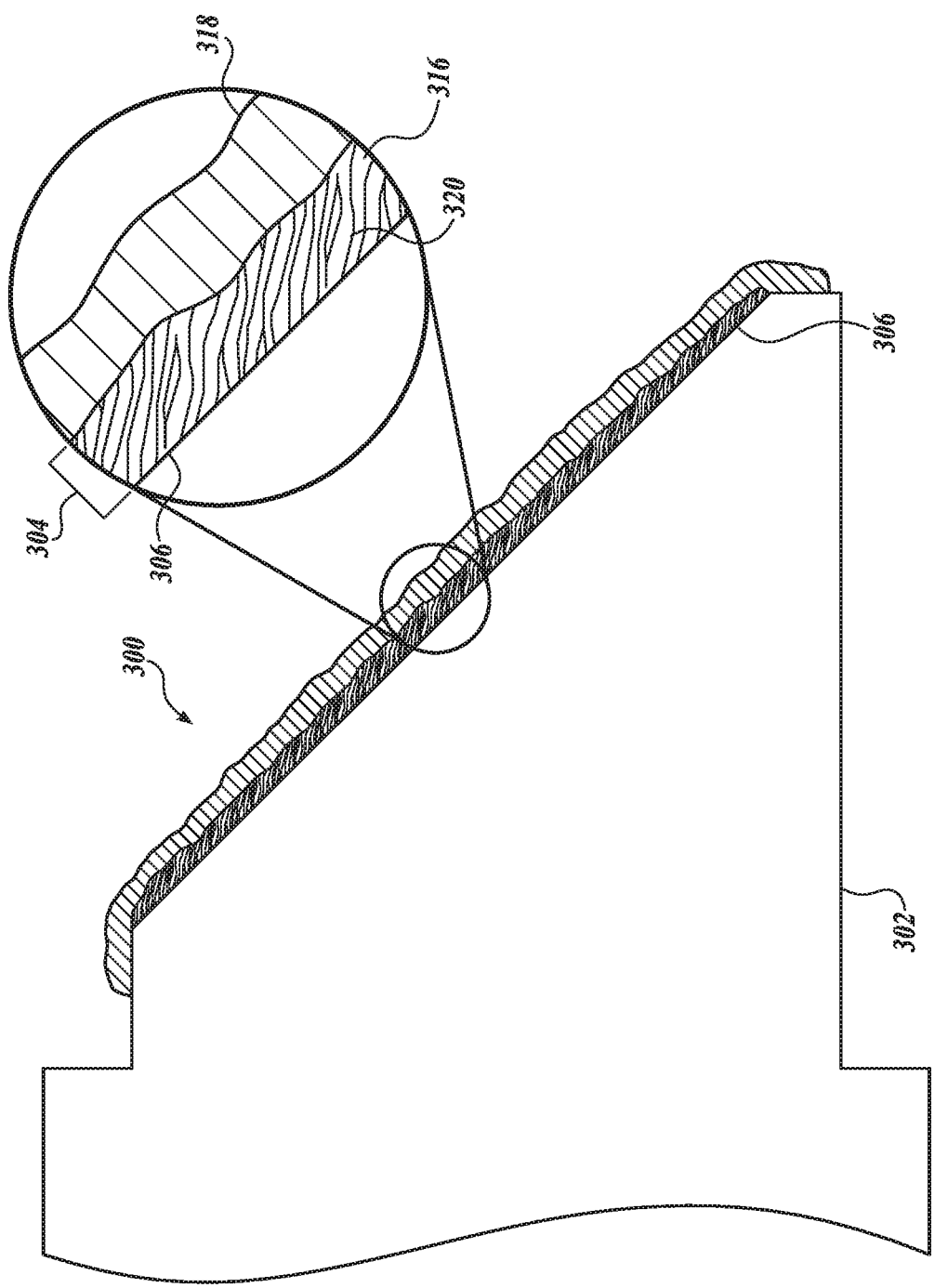
FIG. 3C is a cross-sectional illustration of a portion of another intraocular lens including a reinforcing layer including fibers disposed on an inner surface of an annular body, in accordance with an embodiment of the disclosure.

Still referring to FIG. 3C, in an embodiment, the dielectric layer 318 entirely covers the flexible conductor 316, which is in direct contact with the fibers 320. By entirely covering the flexible conductor 316 with the dielectric layer 318, electrical shorts are prevented. Such a configuration can be useful where conductive fibers, such as carbon nanotubes, silver nanowires, and the like, are used in the reinforcing layer 304.

In an embodiment, the reinforcing layer of an IOL of the present disclosure is embedded in a portion of flexible material of an annular body of the IOL proximate to an inner surface of the IOL. In that regard, attention is directed to FIG. 3D, which is a cross-sectional illustration of a portion of an IOL 300 including a reinforcing layer 304 embedded in a portion of an annular body 302 proximate to a surface 306 of the annular body 302, in accordance with an embodiment of the disclosure. In the illustrated embodiment, the reinforcing layer 304 includes fibers 320 embedded in a portion of the annular body 302 proximate to an inner surface 306 of the annular body 302. In an embodiment, the portion of the annular body 302 proximate to the inner surface 306 comprises a flexible material. In an embodiment, the portion of the flexible conductor 316 is directly disposed onto the inner surface 306 of the annular body 302 and between dielectric layer 318. As described further herein with respect to method 500, in an embodiment such a configuration can be made by applying reinforcing layer 304 materials, such as fibers 320, on a portion of a mold configured to form an inner surface 306 of the annular body 302. The flexible material is then cast over the reinforcing layer materials.

In an embodiment, a reinforcing layer of an IOL of the present disclosure comprises particles. In that regard attention is directed to FIG. 3E, which is a cross-sectional illustration of a portion of another IOL 300 including a reinforcing layer 304 including particles 326 disposed on an inner surface 306 of an annular body 302, in accordance with an embodiment of the disclosure. As illustrated IOL 300 includes a reinforcing layer 304 carried by an inner surface 306 of the annular body 302, a flexible conductor 316 carried by at least a portion of the reinforcing layer, and a dielectric layer 318 disposed over the flexible conductor 316. Further, in the present embodiment, reinforcing layer 304 includes particles 326 embedded in a polymeric matrix 324.

As discussed elsewhere herein, during insertion IOL 300 may be rolled, bent, or otherwise deformed during implantation, thereby inducing stress on certain portions of the IOL 300. While certain portions of the IOL 300 experience tensile stress other portions are under compressive stress, as discussed further herein with respect to FIG. 4. Fibers and certain polymer layers, such as those discussed herein with respect to certain reinforcing layers 304, are generally resistant to stretching. However, some fibers and polymer layers are less resistant to compressive stress. In certain embodiments, reinforcing layer 304 including particles, such as particles 326, is configured to withstand compressive stress and thereby mitigate or prevent cracking or delamination of a flexible conductor 316.

In an embodiment, the particles 326 include glass beads. In an embodiment, the particles 326 comprise nanoparticles 326 having an average smallest dimension less than one micron. In an embodiment, the particles 326 comprise microparticles 326 having an average smallest dimension of 100 nanometers or less.

In an embodiment, the particles 326 have irregular shapes configured to interlock with one another when compressed, thereby providing greater compressive strength.

Figure 3D:
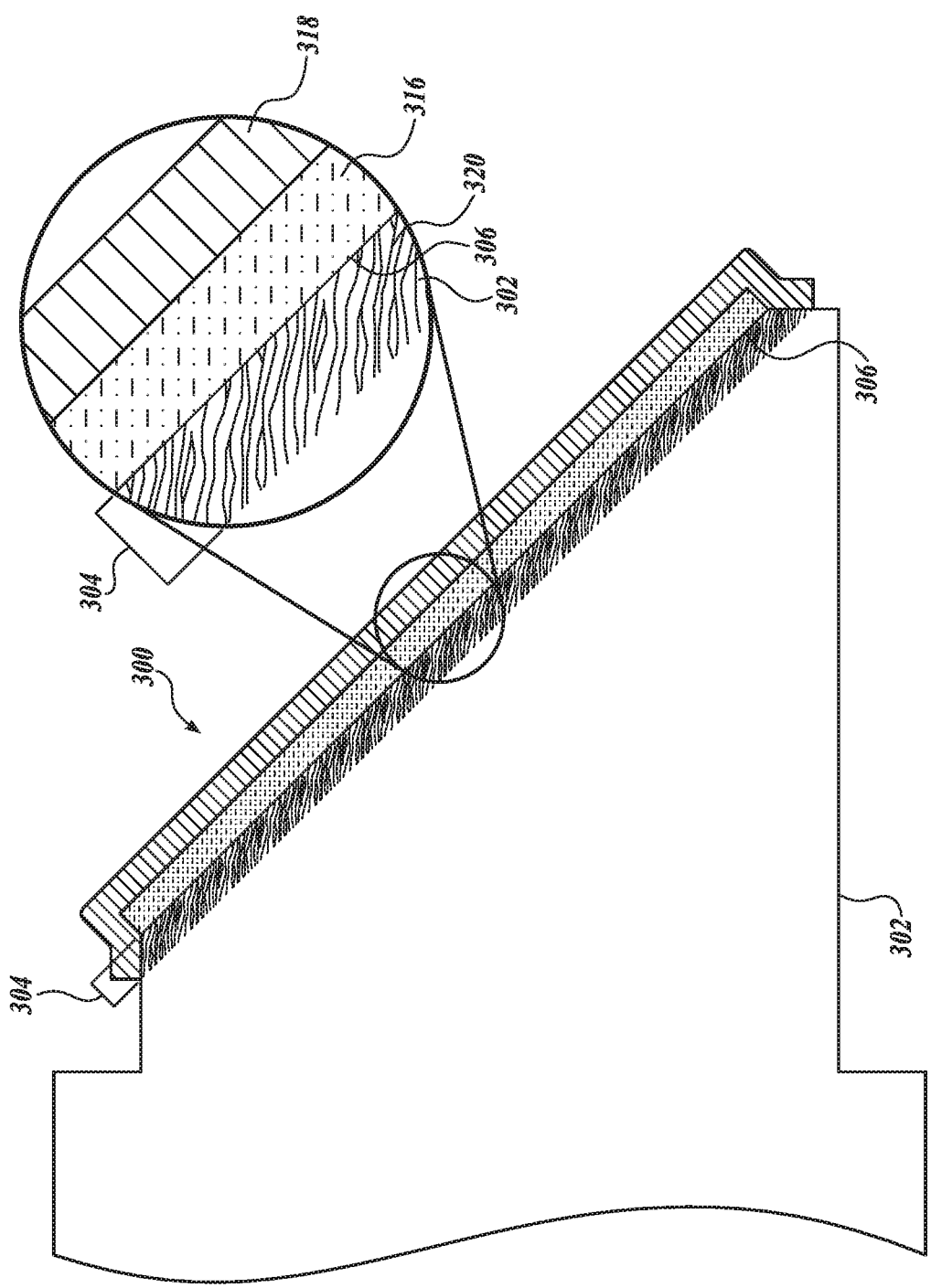
FIG. 3D is a cross-sectional illustration of a portion of an intraocular lens including a reinforcing layer embedded in a portion of an annular body proximate to a surface of the annular body, in accordance with an embodiment of the disclosure.
Figure 3E:
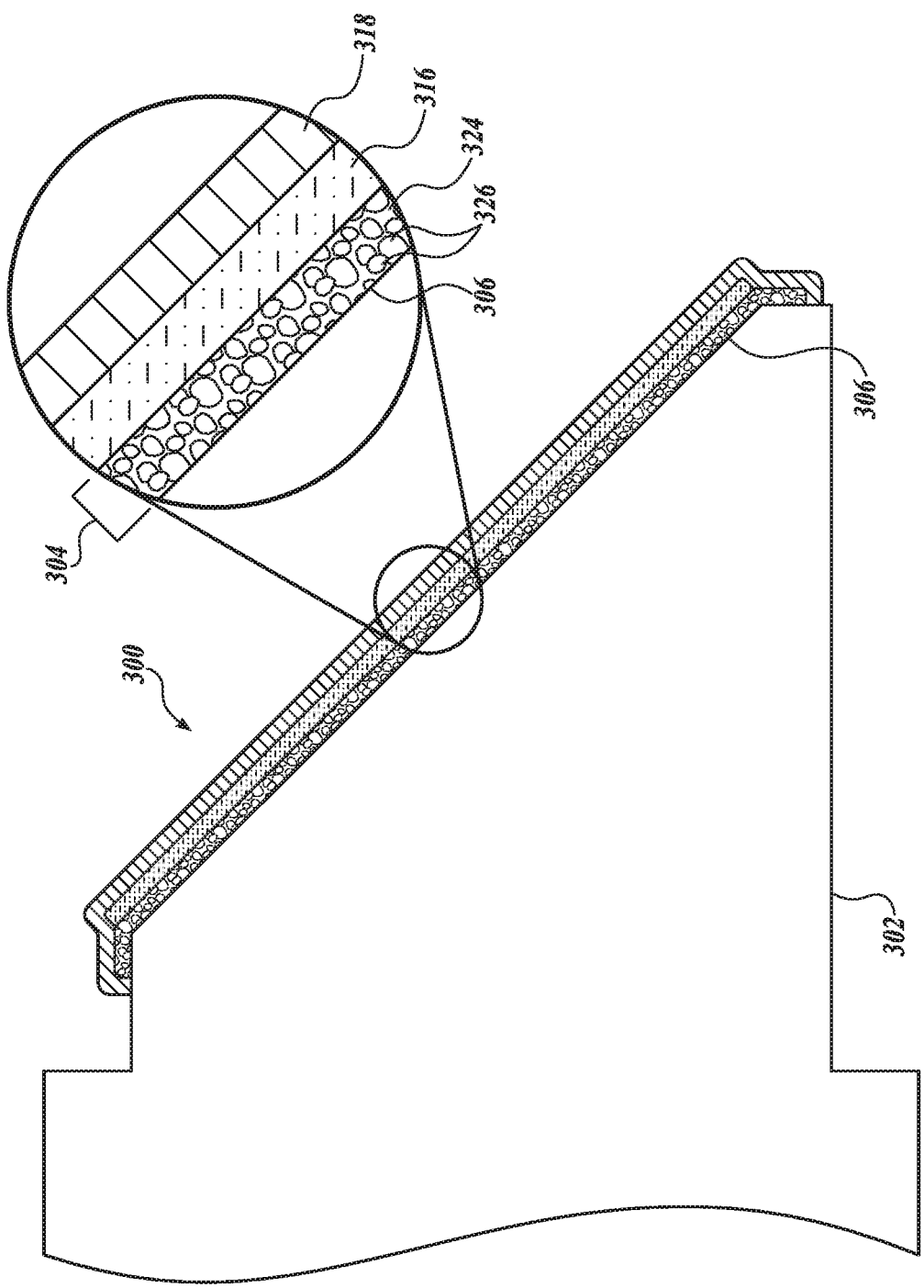
FIG. 3E is a cross-sectional illustration of a portion of another intraocular lens including a reinforcing layer including particles disposed on an inner surface of an annular body, in accordance with an embodiment of the disclosure.

In an embodiment, the reinforcing layer 304 includes particles 326 and fibers, such as those discussed further herein with respect to FIGS. 3B and 3D, embedded in a polymeric matrix 324.

Figure 6:
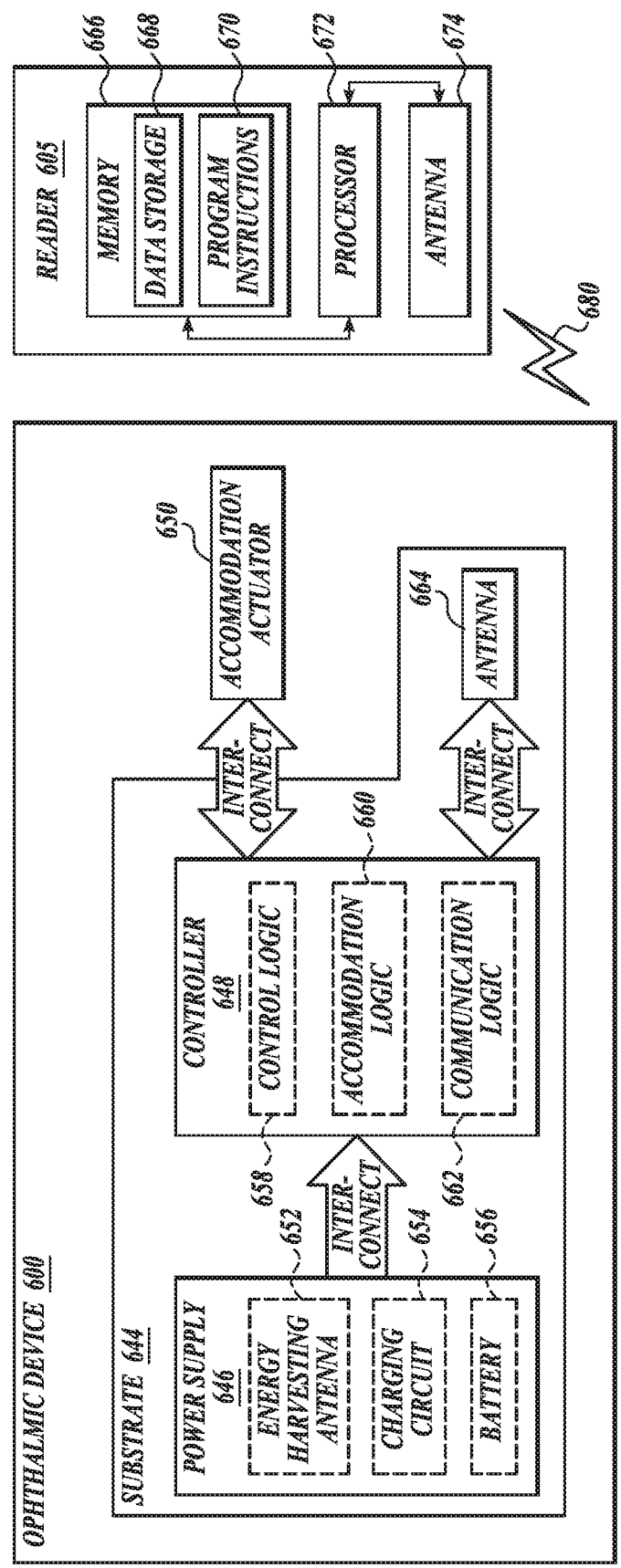
FIG. 6 is a functional block diagram of an ophthalmic device including a reinforcing layer, in accordance with an embodiment of the present disclosure.

FIG. 6 is a functional block diagram of an ophthalmic device 600 including a reinforcing layer, in accordance with an embodiment of the present disclosure. Ophthalmic device 600 may be an implantable device, such as an IOL. In an embodiment, ophthalmic device 600 is an example of IOLs 100, 200, 300, 400, and 700. In the depicted embodiment, ophthalmic device 600 includes a substrate 644 configured to be implanted into an eye. The substrate 644 is configured to provide a mounting surface for a power supply 646, a controller 648, an antenna 664, and various interconnects. The substrate 644 and the associated electronics may be one implementation of the control electronics 126 and an associated annular ring, such as the annular body 102. The illustrated embodiment of power supply 646 includes an energy harvesting antenna 652, charging circuitry 654, and a battery 656. The illustrated embodiment of controller 648 includes control logic 658, accommodation logic 660, and communication logic 662.

Power supply 646 supplies operating voltages to the controller 648 and/or the accommodation actuator 650. Antenna 664 is operated by the controller 648 to communicate information to and/or from ophthalmic device 600. In the illustrated embodiment, antenna 664, controller 648, and power supply 646 are disposed on/in substrate 644. In one embodiment, accommodation actuator 650 is disposed on an inner surface of the substrate 644, such as the inner surface 206 of annular body 202, and includes a flexible conductor, such as the flexible conductors 216, 316, and/or 416.

Substrate 644 includes one or more surfaces suitable for mounting controller 648, power supply 646, and antenna 664. Substrate 644 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 644 to form circuitry, electrodes, etc. For example, antenna 664 can be formed by depositing a pattern of gold or another conductive material on substrate 644. Similarly, interconnects can be formed by depositing suitable patterns of conductive materials on substrate 644. A combination of resists, masks, and deposition techniques can be employed to pattern materials on substrate 644. Substrate 644 can be a relatively soft material, such as a polymer or another material sufficient to structurally support the circuitry and/or electronics while being flexible enough to be rolled or folded. Ophthalmic device 600 can alternatively be arranged with a group of unconnected substrates rather than a single substrate 644. For example, controller 648 and power supply 646 can be mounted to one substrate 644, while antenna 664 is mounted to another substrate and the two can be electrically connected via interconnects.

Substrate 644 can be shaped as a flattened ring with a radial width dimension sufficient to provide a mounting platform for the embedded electronic components. Substrate 644 can have a thickness sufficiently large to provide structural stability suitable for supporting the electronics mounted thereon. For example, substrate 644 can be shaped as a ring with a diameter of about 10 millimeters, a radial width of about 1 millimeter (e.g., an outer radius 1 millimeter larger than an inner radius), and a thickness of about 50 micrometers. In some embodiments, the substrate 644 may encircle at least the optical area associated with the accommodation actuator 650, and may be analogous to the annular bodies 102 and/or 202. For example, the substrate 644 may be disposed in a peripheral area and in between at least two optical elements, such as optical windows 208 and 210.

In the illustrated embodiment, power supply 646 includes a battery 656 to power the various embedded electronics, including controller 648. Battery 656 may be inductively charged by charging circuitry 654 and energy harvesting antenna 652. In one embodiment, antenna 664 and energy harvesting antenna 652 are independent antennae, which serve their respective functions of energy harvesting and communications. In another embodiment, energy harvesting antenna 652 and antenna 664 are the same physical antenna that are time shared for their respective functions of inductive charging and wireless communications with reader 605.

Additionally or alternatively, power supply 646 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 654 may include a rectifier/regulator to condition the captured energy for charging battery 656 and/or directly power controller 648. Charging circuitry 654 may also include one or more energy storage devices to mitigate high frequency variations in energy harvesting antenna 652. For example, one or more energy storage devices (e.g., a capacitor, an inductor, etc.) can be connected to function as a low-pass filter.

Controller 648 contains logic to choreograph the operation of the other embedded components. Control logic 658 controls the general operation of ophthalmic device 600, including providing a logical user interface, power control functionality, etc. Accommodation logic 660 includes logic for receiving signals from sensors monitoring the orientation of the eye, determining the current gaze direction or focal distance of the user, and manipulating accommodation actuator 650 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 662 provides communication protocols for wireless communication with reader 605 via antenna 664. In one embodiment, communication logic 662 provides backscatter communication via antenna 664 when in the presence of an electromagnetic field 680 output from reader 605. In one embodiment, communication logic 662 operates as a smart wireless radio-frequency identification ("RFID") tag that modulates the impedance of antenna 664 for backscatter wireless communications. The various logic modules of controller 648 may be implemented in software/firmware executed on a general purpose microprocessor, in hardware (e.g., application specific integrated circuit), or a combination of both.

Ophthalmic device 600 may include various other embedded electronics and logic modules. For example, a light source or pixel array may be included to provide visible feedback to the user. An accelerometer or gyroscope may be included to provide positional, rotational, directional or acceleration feedback information to controller 648.

The illustrated embodiment also includes reader 605 with a processor 672, an antenna 674, and memory 666. Memory 666 in reader 605 includes data storage 668 and program instructions 670. As shown reader 605 may be disposed outside of ophthalmic device 600, but may be placed in its proximity to charge ophthalmic device 600, send instructions to ophthalmic device 600, and/or extract data from ophthalmic device 600. In one embodiment, reader 605 may resemble a conventional contact lens holder that the user places ophthalmic device 600 in at night to charge, extract data, clean the lens, etc.

External reader 605 includes antenna 674 (or group of more than one antenna) to send and receive wireless signals 680 to and from ophthalmic device 600. External reader 605 also includes a computing system with processor 672 in communication with memory 666. Memory 666 is a non-transitory computer-readable medium that can include, without limitation, magnetic disks, optical disks, organic memory, and/or any other volatile (e.g., RAM) or non-volatile (e.g., ROM) storage system readable by the processor 672. Memory 666 can include a data storage 668 to store indications of data, such as data logs (e.g., user logs), program settings (e.g., to adjust behavior of ophthalmic device 600 and/or external reader 605), etc. Memory 666 can also include program instructions 670 for execution by processor 672 to cause the external reader 605 to perform processes specified by the instructions 670. For example, program instructions 670 can cause external reader 605 to provide a user interface that allows for retrieving information communicated from ophthalmic device 600 or allows transmitting information to ophthalmic device 600 to program or otherwise select operational modes of ophthalmic device 600. External reader 605 can also include one or more hardware components for operating antenna 674 to send and receive wireless signals 680 to and from ophthalmic device 600.

External reader 605 can be a smart phone, digital assistant, or other portable computing device with wireless connectivity sufficient to provide the wireless communication link 680. External reader 605 can also be implemented as an antenna module that can be plugged into a portable computing device, such as in an embodiment where the communication link 680 operates at carrier frequencies not commonly employed in portable computing devices. In some instances, external reader 605 is a special-purpose device configured to be worn relatively near a wearer's eye to allow the wireless communication link 680 to operate with a low power budget. For example, the external reader 605 can be integrated in a piece of jewelry such as a necklace, earring, etc. or integrated in an article of clothing worn near the head, such as a hat, headband, etc.

While annular bodies being annulus-shaped are described herein, other embodiments provide lens bodies having other shapes other than annuli. For example, in certain embodiments according to the present disclosure, the intraocular lens includes bodies formed from a flexible material having a shape suitable for forming an intraocular lens other than an annulus. Such shapes can include, without limitation, a disc, a lens, a regular polygon, an irregular polygon, a free shape, and the like.

While accommodating intraocular lenses including reinforcing layers have been described herein, it will be understood that the reinforcing layers described herein may be applied to and included in other designs and configurations of intraocular lenses in accordance with embodiments of the present disclosure. Further, while accommodating intraocular lenses including reinforcing layers have been described herein, it will be understood that the reinforcing layers described herein may be applied to and included in other ophthalmic devices. Such other ophthalmic device can include, for example, contact lenses.

Figure 5:
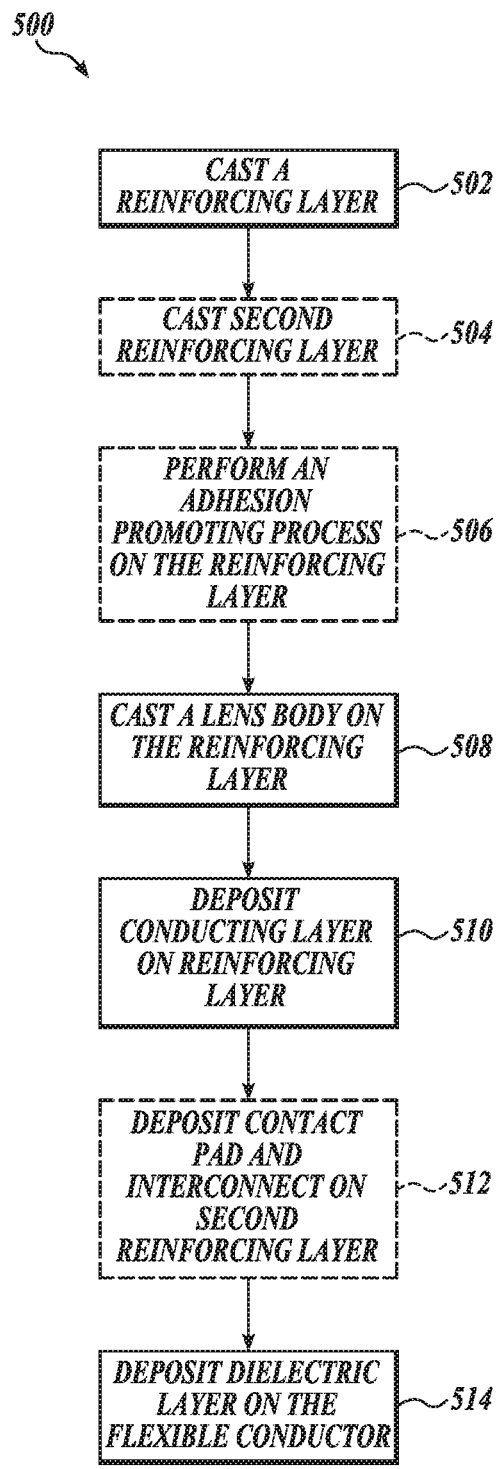
FIG. 5 is a schematic illustration of an exemplary method for making an intraocular lens including a reinforcing layer, in accordance with an embodiment of the disclosure.

In another aspect, the present disclosure provides a method for making an intraocular lens including a reinforcing layer. In that regard, attention is directed to FIG. 5, which is a schematic illustration of an exemplary method 500 for making an intraocular lens including a reinforcing layer, in accordance with an embodiment of the disclosure. The method 500 may be an example process for forming at least a portion of an intraocular lens, such as the IOLs 100, 200, 300, 400, 600, and 700. The order in which some or all of the process blocks appear in method 500 should not be deemed limiting. Rather, one of ordinary skill in the art having the benefit of the present disclosure will understand that some of the method blocks may be executed in a variety of orders not illustrated, or even in parallel.

The method may begin with process block 502, which includes casting a reinforcing layer, such as in a mold configured to form at least a portion of an intraocular lens shaped to cover an inner surface and/or optical window of the intraocular lens. In an embodiment, casting the reinforcing layer includes spray coating or otherwise depositing a portion of the mold with a solution or suspension including reinforcing layer reagents. In an embodiment, the solution or suspension including reinforcing layer reagents includes a polymer having a higher elastic modulus than a flexible material used, for example, for an annular body as discussed further herein. In an embodiment, the polymer is a molten polymer and the molten polymer is cast by spray coating. In an embodiment, the solution or suspension including reinforcing layer reagents includes fibers, such as nanofibers. In an embodiment, the solution or suspension including reinforcing layer reagents includes particles, such as nanoparticles.

In an embodiment, casting the reinforcing layer includes spin casting or dip casting a solution or suspension of reinforcing layer reagents onto at least a portion of the mold. In an embodiment, the reinforcing layer reagents include polyetherimide and a solvent including n-methyl-2-pyrrolidone.

In an embodiment, the solution or suspension including reinforcing layer reagents includes a carrier fluid. After initial application or deposition of the solution or suspension, the carrier fluid evaporates leaving a reinforcing layer. In an embodiment, the carrier fluid includes reagents suitable to create a polymer matrix. After initial application or deposition of the solution or suspension, the reagents form a polymer matrix into which, for example, the reinforcing layer reagents, such as fibers and/or particles, are embedded, as discussed further herein with respect to FIGS. 3B and 3E. In an embodiment, the fibers are fibers 320. In an embodiment, the particles are particles 326.

In some embodiments, the mold may be masked such that only a portion of the mold is exposed during depositing of the reinforcing layer. In some embodiments, the mask may include openings for at least a second reinforcing layer.

In an embodiment, the reinforcing layer is cast on a portion of the mold configured to form a portion of the IOL including an optical path, such as an optical window. In an embodiment, the reinforcing layer includes fibers, such as nanofibers, as discussed further herein with respect to FIG. 3B.

Process block 502 may be followed by process block 504, which includes casting a second reinforcing layer. As discussed further herein, in certain embodiments the IOLs of the present disclosure include two or more reinforcement layers configured to carry, for example, contact pads, interconnects, control electronics, and other electronic components. Casting the second reinforcing layer can include, for example, the methods useful for depositing the first reinforcing layer, a described herein with respect to process block 502. In some embodiments, block 504 is optional.

Process block 502 or process block 504 may be followed by process block 506, which includes performing an adhesion promoting process on at least the reinforcing layer. The adhesion promoting process may include a cleaning or surface treatment, such as treatment with an oxygen plasma, to alter a surface energy of the reinforcing layer, or it may include the deposition of a thin film of an adhesion promoting substance that may be cannibalized by a subsequent process block. In some embodiments, process block 506 is optional.

In an embodiment, the adhesion promoting process includes partially curing a reinforcing layer including curable polymer. By partially curing the reinforcing layer the reinforcing layer is at least temporarily a tacky solid or semi-solid and adheres to subsequently added layers, such as flexible materials suitable for forming an annular body. In an embodiment, partially curing a reinforcing layer includes exposing a UV-curable liquid to ultraviolet light for a period of time sufficient to provide a tacky solid or semisolid, such as for a time between 1-30 seconds. Such a UV-curable solution or suspension includes solutions or suspensions including a UV-curable acrylate, a UV-curable thiol-ene, a UV-curable epoxy, and combinations thereof.

Process block 502, process block 504, or process block 506 may be followed by process block 508, which includes casting a lens body from a flexible material on at least a portion of the reinforcing layer. In an embodiment, casting the lens body includes casting an annular body being annulus shaped from a flexible material on at least a portion of the reinforcing layer. As discussed further herein, in an embodiment, the reinforcing layer has a higher elastic modulus than the flexible material. In an embodiment, the annular body is an annular body such as annular bodies 102, 202, 302, 402, and 702.

In an embodiment, casting the annular body provides an annular body having at least one inner surface, e.g., a sidewall that defines an aperture through the annular body. The at least one inner surface may have a conical frustum shape such that the inner surface is at an oblique or non-normal angle to anterior and posterior surfaces of the annular body. In some embodiments, the at least one inner surface may be at 45° to the anterior and posterior surfaces. In an embodiment, the annular body is coupled to a portion of the reinforcing layer at an inner surface of the annular body. In an embodiment, casting the annular body also includes casting an optical window, such as an optical window discussed further herein with respect to FIG. 2, along with the annular body.

In an embodiment, process block 508 precedes process block 502. In that regard, in an embodiment, the method 500 may begin with block 508, including casting a lens body from a flexible material. In an embodiment, process block 508 is followed by process block 502, including casting a reinforcing layer on at least a portion of the lens body. Casting the reinforcing layer on at least a portion of the lens body may be accomplished according to any of the deposition methods described elsewhere herein.

Process block 508 may be followed by process block 510, including depositing a conductor to a portion of the reinforcing layer. In an embodiment, the conductor is a flexible conductor. In an embodiment, the conductor is a ductile conductor. In some embodiments, it may be desirable for the conductor to be self-healing; that is, a flexible conductor that automatically repairs damage to itself without any external diagnosis of the problem or human intervention. In an embodiment, depositing a self-healing conductor includes depositing a layer of a metal chosen from aluminum, titanium, tantalum, niobium, vanadium, hafnium, tungsten, zirconium, molybdenum, and combinations thereof.

In an embodiment, depositing the conductor includes sputtering the flexible conductor material on at least a portion of the reinforcing layer. In an embodiment, depositing the conductor includes evaporating flexible conductor material on at least a portion of the reinforcing layer. In an embodiment, depositing the conductor includes chemical vapor deposition of flexible conductor material on at least a portion of the reinforcing layer. In an embodiment, depositing the conductor includes atomic layer deposition of conductor material on at least a portion of the reinforcing layer.

In an embodiment, depositing a conductor to a portion of the reinforcing layer includes depositing a conductor directly onto one or more fibers of the reinforcing layer. In this regard, the one or more fibers of the reinforcing layer are coated or partially covered by the conductor, as described further herein with respect to and illustrated in FIG. 3C.

Process block 510 may be followed by process block 512, which includes depositing a contact pad and an interconnect on at least a portion of the second reinforcing layer, wherein the contact pad and interconnect comprise a flexible, electrically conductive material. Process block 512, which may be optional, may be performed to provide an interconnect to the conductor. Process block 512 may be optionally combined with process block 510 to provide both a flexible and/or ductile conductor on the first reinforcing layer and a contact pad and interconnect on the second reinforcing layer. Alternatively, process blocks 510 and 512 may be performed separately.

By depositing the contact pad and interconnect on the second reinforcing layer having a higher elastic modulus than the flexible material, the contact pad and interconnect are protected from cracking and delamination from the lens body in an analogous way to the protection provided by the first reinforcing layer to the flexible conductor. In an embodiment, depositing the contact pad and interconnect is performed according the methods of depositing the conductor, as described elsewhere herein. In an embodiment, process block 512 is optional.

Process block 512 may be followed by process block 514, which includes depositing a dielectric layer at least on the conductor. The dielectric may be a polymer-based dielectric and may be deposited, for example, using a vapor deposition technique. It may be desirable for the dielectric to conformally coat at least the conductor to prevent electrical shorts between the conductor and other portions of the IOL. Further, it may be desirable that the dielectric layer be transparent and flexible and to provide a chemical barrier to the conductor. In some embodiments, the dielectric layer may be comprise Parylene-C, and have a thickness of 0.5 microns to 4 microns. In an embodiment, the dielectric layer has a thickness of 25 µm. Other example dielectric materials of the dielectric layer may include Parylene-N, Parylene-D, Parylene-HT, Parylene-AF4, and combinations thereof. In other embodiments the dielectric layer may comprise a silicone.

While illustrative embodiments have been illustrated and described, it will be appreciated that various changes can be made therein without departing from the spirit and scope of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An intraocular lens, comprising:
a lens body having at least one inner surface, wherein the lens body is formed from a flexible material amenable to implantation into an eye;
a reinforcing layer carried by the at least one inner surface, wherein a material that forms the reinforcing layer has a higher elastic modulus than the flexible material;
a conductor carried by at least a portion of the reinforcing layer, wherein the conductor is electrically coupled to adjust electrowetting behavior of the intraocular lens; and
a dielectric layer disposed over the conductor.

2. The intraocular lens of claim 1, wherein the conductor covers less than all of the reinforcing layer.

3. The intraocular lens of claim 1, wherein the lens body has an anterior side and a posterior side and recesses formed in the anterior and posterior sides, wherein the at least one inner surface defines an aperture through the lens body, and wherein the at least one inner surface is at an oblique angle to the anterior and posterior sides of the lens body.

4. The intraocular lens of claim 3, further comprising a first optical window and a second optical window disposed in the recesses formed in the anterior and posterior sides of the lens body, respectively, and covering the aperture.

5. The intraocular lens of claim 4, further comprising two immiscible liquids disposed in the aperture of the lens body, wherein a voltage applied to the conductor alters a wetting characteristic of the dielectric layer to cause an interface between the two immiscible liquids to change an optical power of the intraocular lens.

6. The intraocular lens of claim 1, wherein the reinforcing layer comprises a polymeric material having a higher elastic modulus than the flexible material.

7. The intraocular lens of claim 1, wherein the reinforcing layer comprises fibers.

8. The intraocular lens of claim 7, wherein the fibers are embedded in a polymeric matrix.

9. The intraocular lens of claim 7, wherein the reinforcing layer is embedded in a portion of the flexible material proximate to the at least one inner surface.

10. The intraocular lens of claim 7, wherein the conductor is directly disposed on at least a portion of the fibers.

11. The intraocular lens of claim 7, wherein the fibers have an average smallest dimension of between about 1 nm and about 400 nm.

12. The intraocular lens of claim 1, wherein the reinforcing layer comprises particles embedded in a polymer matrix.

13. The intraocular lens of claim 1, wherein the conductor comprises a self-healing material.

14. The intraocular lens of claim 1, wherein the reinforcing layer is a first reinforcing layer, the intraocular lens further comprising a second reinforcing layer carried by the at least one inner surface and a contact pad and an interconnect carried by the second reinforcing layer, wherein a material that forms the second reinforcing layer has a higher elastic modulus than the flexible material.

15. The intraocular lens of claim 1, wherein the lens body is flexibly capable of being rolled for insertion into an eye, and wherein the conductor does not crack or separate from the reinforcing layer when the intraocular lens is rolled.

* * * * *